United States Patent
O'Dea

(10) Patent No.: US 10,973,998 B2
(45) Date of Patent: Apr. 13, 2021

(54) METHOD AND APPARATUS FOR CONTROLLING INSUFFLATION OF A VESSEL DURING A SURGICAL OR INVESTIGATIVE PROCEDURE AND A SYSTEM AND METHOD FOR INSUFFLATING A VESSEL

(71) Applicant: Palliare Limited, Galway (IE)

(72) Inventor: John O'Dea, Bearna (IE)

(73) Assignee: Palliare Limited, Galway (IE)

(*) Notice: Subject to any disclaimer, the term of this patent is extended or adjusted under 35 U.S.C. 154(b) by 361 days.

(21) Appl. No.: 15/524,383

(22) PCT Filed: Nov. 5, 2015

(86) PCT No.: PCT/IE2015/000017
§ 371 (c)(1),
(2) Date: May 4, 2017

(87) PCT Pub. No.: WO2016/071893
PCT Pub. Date: May 12, 2016

(65) Prior Publication Data
US 2018/0280634 A1 Oct. 4, 2018

(30) Foreign Application Priority Data

Nov. 5, 2014 (IE) .................................... 2014/0277
Nov. 18, 2014 (IE) .................................... 2014/0292

(51) Int. Cl.
*A61M 13/00* (2006.01)

(52) U.S. Cl.
CPC .......... *A61M 13/003* (2013.01); *A61M 13/00* (2013.01); *A61M 2202/0225* (2013.01); *A61M 2205/3344* (2013.01)

(58) Field of Classification Search
CPC .. A61M 13/00; A61M 13/003; A61M 13/006; A61M 5/16854; A61M 5/1723;
(Continued)

(56) References Cited

U.S. PATENT DOCUMENTS 5,328,458 A * 7/1994 Sekino ............... A61M 13/003
604/23
5,423,741 A 6/1995 Frank
(Continued)

FOREIGN PATENT DOCUMENTS

DE 10 2012 110 889 A1 5/2014

OTHER PUBLICATIONS

International Search Report for PCT/IE2015/000017 dated Feb. 4, 2016 [PCT/ISA/210].
(Continued)

*Primary Examiner* — Kami A Bosworth
(74) *Attorney, Agent, or Firm* — Sughrue Mion, PLLC

(57) ABSTRACT

A system for insufflating a vessel in a human or animal body, such as the rectum comprises a first pressure sensor located adjacent a leading end of an endoscope for monitoring pressure in the rectum. A second pressure sensor located on a carrier element which is urgeable through the endoscope into the colon monitors pressure therein. Insufflating air which may leak into the abdominal cavity is exhausted therefrom by a needle. A third pressure sensor monitors pressure in the abdominal cavity. A microcontroller controls the supply of insufflating air to the rectum for maintaining pressure in the rectum at a first predefined pressure, for preventing pressure in the colon exceeding a second predefined pressure, and for controlling a vacuum pump for drawing insufflating air from the abdominal cavity to prevent pressure therein exceeding a third predefined pressure.

17 Claims, 5 Drawing Sheets

Figure 1:
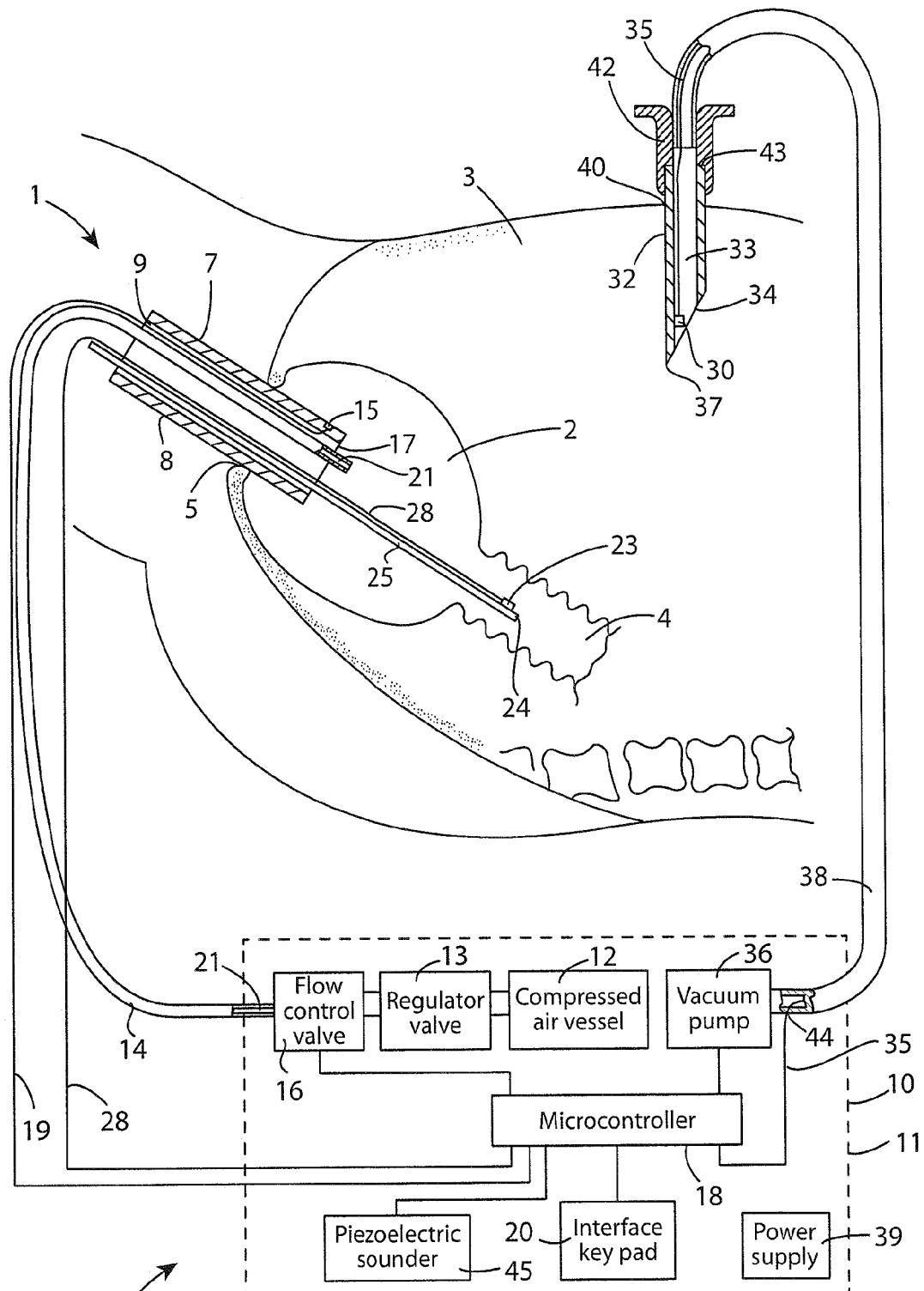

(58) Field of Classification Search
CPC .... A61M 2005/006; A61M 2005/1726; A61M 2025/0001; A61M 2025/0002; A61M 2025/0003; A61M 2202/02; A61M 2025/0208; A61M 2025/0216; A61M 2025/0225; A61M 2025/025–0291; A61M 2205/3331; A61M 2205/3341; A61M 2205/3344; A61B 5/033; A61B 5/035; A61B 5/036; A61B 5/037; A61B 5/038
See application file for complete search history.

(56) References Cited

U.S. PATENT DOCUMENTS

| | | | | |
|---|---|---|---|---|
| 6,299,592 | B1* | 10/2001 | Zander | A61M 13/003 600/560 |
| 2006/0100579 | A1* | 5/2006 | Maahs | A61M 13/003 604/151 |
| 2006/0129087 | A1* | 6/2006 | Uesugi | A61M 13/003 604/26 |
| 2007/0255165 | A1* | 11/2007 | Uesugi | A61B 1/00135 600/560 |
| 2009/0124999 | A1* | 5/2009 | Horton | A61M 25/0068 604/514 |
| 2011/0218484 | A1* | 9/2011 | Zemlok | A61M 13/00 604/26 |
| 2013/0123682 | A1 | 5/2013 | Costovici | |
| 2014/0236074 | A1 | 8/2014 | Faif et al. | |
| 2015/0148836 | A1* | 5/2015 | Heeren | A61F 9/00763 606/170 |

OTHER PUBLICATIONS

Written Opinion for PCT/IE2015/000017 dated Feb. 4, 2016 [PCT/ISA/237].

* cited by examiner

METHOD AND APPARATUS FOR CONTROLLING INSUFFLATION OF A VESSEL DURING A SURGICAL OR INVESTIGATIVE PROCEDURE AND A SYSTEM AND METHOD FOR INSUFFLATING A VESSEL

CROSS REFERENCE TO RELATED APPLICATIONS

This application is a National Stage of International Application No. PCT/IE2015/000017 filed Nov. 5, 2015, claiming priority based on Irish Patent Application Nos. S2014/0277 filed Nov. 5, 2014 and S2014/0292 filed Nov. 18, 2014, the contents of all of which are incorporated herein by reference in their entirety.

The present invention relates to apparatus for controlling insufflation of a vessel, lumen or cavity during a surgical or investigative procedure in the body of a human or animal subject. The invention also relates to a method for controlling insufflation of a vessel, lumen or cavity during a surgical or investigative procedure in the body of a human or animal subject. Further, the invention relates to a system and a method for insufflating a vessel, lumen or cavity in the body of a human or animal subject.

Throughout this specification the use of the term "vessel" is intended to include a vessel, lumen, cavity and other such vessel in the body of a human or animal subject.

During an investigative and surgical procedure in a vessel in a human or animal body which is carried out by an imaging device and/or surgical instruments which are passed into the vessel through an endoscope or a laparoscope or other such insertion element for accommodating instruments into the vessel, the vessel is insufflated with a fluid inflating medium for maintaining the vessel inflated to facilitate the investigative or surgical procedure. The fluid inflating medium, in general, is a gas such as carbon dioxide or air, but may be other suitable gases. However, the fluid inflating medium may also be liquid, such as a saline solution, water or other suitable liquid. Indeed, more recently in investigative and surgical procedures in the colon, it is common to insufflate the colon with a liquid. In cases where the fluid inflating medium is a gas, the gas for insufflating a vessel may be derived from a compressed gas source or a pumped gas source. Where the inflating medium is carbon dioxide, the carbon dioxide, in general, is provided from a source of compressed carbon dioxide. The carbon dioxide from the compressed source thereof is delivered to the vessel through a pressure regulating valve and a flow control valve, in order to regulate the pressure and the flow rate at which the carbon dioxide gas is delivered to the vessel. In the case of air being the inflating medium, the air may be provided from a compressed air source, and delivered to the vessel through a pressure regulating valve and a flow control valve, similarly for regulating the pressure and the flow rate at which the air is delivered to the vessel. Alternatively, the air inflating medium may be provided by an air pump or an air blower. In general, a liquid inflating medium is provided from a pumped source of the liquid medium. The inflating medium, be it a gas or a liquid, in general, is delivered to the vessel through a conduit, which in turn is passed into the vessel through the bore of the endoscope or laparoscope.

However, it is essential that the vessel in which the procedure is being carried out should not be over or hyper-inflated, but at the same time should be maintained inflated at a suitable pressure to avoid collapsing of the vessel during the procedure. Additionally, due to leaking of the inflating medium from the vessel, either through the bore of the endoscope or laparoscope or along the outer surface of the endoscope or laparoscope, pressure may also fall in the vessel, thus leading to the collapse of the vessel. Such leaking of inflating medium from a vessel may also occur through a vessel wall, as a result of an incision made during surgery in the vessel. This requires monitoring of the pressure of the inflating medium with which the vessel is being inflated.

In general, a pressure sensor is located externally of the vessel and externally of the body of the subject, and typically, the pressure sensor is located in the conduit through which the inflating medium is being delivered to the vessel, and in general, the pressure sensor is located in the conduit adjacent the source from which the inflating medium is provided. However, since the inflating medium source is normally located some distance from the vessel, which is being insufflated, a pressure drop results from the pressure sensor to the vessel. Thus, in order to determine the pressure of the inflating medium in the vessel which is being insufflated, it is necessary to compensate for the pressure drop from the pressure sensor to the vessel. This requires computing the pressure drop which is a function to the product of the flow of the inflating medium through the conduit through which the inflating medium is delivered to the vessel and the resistance to flow of the inflating medium through the conduit plus the length of the conduit. The computed pressure drop must then be subtracted from the pressure read by the pressure sensor. Since the flow rate of the inflating medium may fluctuate, and in particular, since the resistance to flow of the inflating medium in the conduit may, and in general, will always vary as a result of bends, kinks and the like in the conduit, it is difficult, if not impossible, to obtain a true value of the pressure in the vessel which is being insufflated during insufflating thereof. This is undesirable.

The present invention is directed towards providing apparatus for controlling insufflation of a vessel in the body of a human or animal subject which addresses this problem. The invention is also directed towards providing a method for controlling insufflation of a vessel in the body of a human or animal subject which addresses the problem. Additionally, the invention is directed towards a system for insufflating a vessel in the body of a human or animal subject, and further the invention is directed towards providing a method for insufflating a vessel in the body of a human or animal subject.

According to the invention there is provided apparatus for controlling insufflation of a vessel in the body of a human or animal subject with a fluid inflating medium, the apparatus comprising a primary pressure sensing means configured for monitoring the pressure of the inflating medium in the vessel, and a control means for controlling delivery of the inflating medium to the vessel in response to the pressure thereof monitored by the primary pressure sensing means.

In one aspect of the invention the primary pressure sensing means is adapted for monitoring the pressure of the inflating medium directly in the vessel. Preferably, the primary pressure sensing means is located for monitoring the pressure of the inflating medium directly in the vessel.

In another aspect of the invention the control means is responsive to the pressure of the inflating medium in the vessel monitored by the primary pressure sensing means for controlling delivery of the inflating medium to the vessel for maintaining the pressure of the inflating medium in the vessel substantially at a primary predefined pressure.

Preferably, the primary pressure sensing means is configured for monitoring the pressure of the inflating medium in the vessel adjacent a leading end of a primary insertion element adapted for insertion into the vessel to accommodate instruments therethrough into the vessel.

In another aspect of the invention an elongated inflating conduit having a bore extending therethrough is provided for delivering the inflating medium into the vessel, the inflating conduit terminating in a first end through which the inflating medium is delivered into the vessel. Preferably, the inflating conduit is adapted for one of mounting on the primary insertion element and extending through a bore of the primary insertion element.

In another aspect of the invention the inflating conduit is configured for mounting on the primary insertion element with the first end thereof adjacent the leading end of the primary insertion element.

In a further aspect of the invention the inflating conduit is configured for mounting on the primary insertion element on an outer surface thereof. Preferably, the inflating conduit is configured for releasably mounting on the primary insertion element. Advantageously, a conduit coupling means is provided for coupling the inflating conduit to the primary insertion element.

In another aspect of the invention the inflating conduit is configured for retrofitting to the primary insertion element.

In another aspect of the invention the primary pressure sensing means is adapted for locating in the vessel.

In one aspect of the invention the primary pressure sensing means is configured for locating on one of the primary insertion element and the inflating conduit.

In another aspect of the invention the primary pressure sensing means is configured for mounting on the primary insertion element adjacent the leading end thereof.

In another aspect of the invention the primary pressure sensing means is adapted for releasable mounting on the primary insertion element.

In a further aspect of the invention the primary pressure sensing means is configured for inserting into the vessel through a bore in the primary insertion element.

In another aspect of the invention the primary pressure sensing means is located in the inflating conduit adjacent the first end of the inflating conduit.

In a further aspect of the invention the primary pressure sensing means is located in the bore of the inflating conduit through which the inflating medium is delivered to the vessel.

In another aspect of the invention the primary pressure sensing means is adapted for mounting in the bore extending through the primary insertion element.

In an alternative aspect of the invention the primary pressure sensing means is adapted for locating remotely of the vessel.

In one embodiment of the invention a primary communicating conduit extending between a first end and a second end and having a bore extending therethrough between the first end and the second end thereof is provided, the first end of the primary communicating conduit being adapted to extend into the vessel, and the second end thereof being coupled to the primary pressure sensing means with the primary pressure sensing means communicating with the bore of the primary communicating conduit, a static fluid being located in the bore of the primary communicating conduit, the pressure of the static fluid in the bore of the primary communicating conduit being indicative of the pressure of the inflating medium in the vessel, and preferably, the primary communicating conduit is configured for locating relative to the primary insertion element so that the first end of the primary communicating conduit extends into the vessel adjacent the leading end of the primary insertion element.

In another aspect of the invention the primary communicating conduit is configured for one of mounting on an outer surface of the primary insertion element and extending through a bore of the primary insertion element. Advantageously, the first end of the primary communicating conduit terminates in a flexible membrane configured to flex relative to the primary communicating conduit in response to pressure fluctuation of the inflating medium in the vessel for in turn proportionately varying the pressure of the static fluid in the bore of the primary communicating conduit.

In another aspect of the invention the primary pressure sensing means comprises a piezoelectric pressure sensor.

In another aspect of the invention the primary pressure sensing means communicates with the control means, and in one aspect of the invention the primary pressure sensing means is hard wired to the control means. Alternatively, the primary pressure sensing means communicates with the control means wirelessly, and preferably, through a first wireless communicating means.

In one aspect of the invention the primary sensing means comprises a primary pressure sensor. Preferably, the primary sensing means comprises a miniature pressure sensor. Advantageously, the primary pressure sensing means is located in a remote housing adapted for locating in an environment external of the body of the subject.

In another aspect of the invention an adjacent vessel pressure sensing means is provided for monitoring the pressure of the inflating medium in a vessel adjacent to the vessel being insufflated and communicating with the vessel being insufflated, the control means being responsive to the pressure of the inflating medium monitored by the adjacent vessel pressure sensing means for one of producing an alarm signal in response to the pressure monitored by the adjacent vessel pressure sensing means reaching an adjacent vessel predefined pressure, and controlling delivery of the inflating medium to the vessel being insufflated for preventing the pressure in the adjacent vessel exceeding the adjacent vessel predefined pressure.

Preferably, the adjacent vessel pressure sensing means is adapted for locating in the adjacent vessel.

In one aspect of the invention a carrier element is configured for extending into the vessel being insufflated from the primary insertion element, the carrier element terminating in a first end, and being moveable relative to the primary insertion element for urging the first end of the carrier element into the adjacent vessel, and advantageously, the carrier element is adapted for urging through a bore of the primary insertion element, and preferably, the adjacent vessel pressure sensing means is mounted on the carrier element adjacent the first end of the carrier element.

In an alternative embodiment of the invention the adjacent vessel pressure sensing means is located remotely of the adjacent vessel. Preferably, an adjacent vessel communicating conduit extending between a first end and a second end and having a bore extending therethrough between the first end and the second end is provided, the first end of the adjacent vessel communicating conduit being configured to extend into the adjacent vessel, and the second end being coupled to the adjacent vessel pressure sensing means with the adjacent vessel pressure sensing means communicating with the bore extending through the adjacent vessel communicating conduit, and a static fluid located in the bore of the adjacent vessel communicating conduit, the pressure of the static fluid in the bore of the adjacent vessel communicating conduit being indicative of the pressure of the inflating medium in the adjacent vessel. Advantageously, the adjacent vessel communicating conduit terminates at its first end in a flexible membrane configured to flex relative to the adjacent vessel communicating conduit for altering the pressure of the static fluid in the bore thereof in proportion to the pressure of the inflating medium in the adjacent vessel in response to pressure fluctuations of the inflating medium in the adjacent vessel. Preferably, the adjacent vessel communicating conduit is carried on the carrier element, the first end of the adjacent vessel communicating conduit being located adjacent the first end of the carrier element.

In an alternative aspect of the invention the adjacent vessel communicating conduit is configured for mounting on an outer surface of the primary insertion element.

In another aspect of the invention a second coupling means is provided for coupling the adjacent vessel communicating conduit to the primary insertion element, and preferably, the second coupling means comprises a releasable second coupling means for releasably engaging the first primary insertion element.

In one aspect of the invention the adjacent vessel pressure sensing means communicates with the control means. In one aspect of the invention the adjacent vessel pressure sensing means is hardwired to the control means. Alternatively, the adjacent vessel pressure sensing means communicates with the control means wirelessly, and preferably, through a second wireless communicating means.

In one aspect of the invention the adjacent vessel pressure sensing means comprises a pressure sensor. Preferably, the adjacent vessel pressure sensing means comprises a miniature pressure sensor. Advantageously, the adjacent vessel pressure sensing means comprises a piezoelectric pressure sensor.

In another aspect of the invention the adjacent vessel pressure sensing means is located in the remote housing.

In a further aspect of the invention an external vessel pressure sensing means is provided for monitoring pressure in a vessel external of the vessel being insufflated, and within which the vessel being insufflated is located or is adjoining, the control means being responsive to the external vessel pressure sensing means for one of producing an alarm signal in response to the pressure in the external vessel reaching an external vessel predefined pressure, and controlling one of delivery of the inflating medium to the vessel being insufflated, a vacuum pump communicating with the external vessel, and an exhaust valve communicating with the external vessel for preventing the pressure in the external vessel exceeding the external vessel predefined pressure.

Preferably, the one of the vacuum pump and the exhaust valve is operated under the control of the control means.

In one aspect of the invention the external vessel pressure sensing means is configured to communicate with the external vessel.

In another aspect of the invention the external vessel pressure sensing means is adapted for locating in the external vessel.

Alternatively, the external vessel pressure sensing means is adapted for locating remotely of the external vessel, and preferably, an external vessel communicating conduit extending between a first end and a second end and having a bore extending between the first and second ends thereof, the first end of the external vessel communicating conduit being configured to extend into the external vessel, and the second end being coupled to the external vessel pressure sensing means with the external vessel pressure sensing means communicating with the bore of the external vessel communicating conduit, a static fluid being located in the bore of the external vessel communicating conduit, the pressure in the static fluid in the bore of the external vessel communicating conduit being indicative in the pressure of the external vessel.

In one aspect of the invention a secondary insertion element is provided for inserting into the external vessel to communicate the external vessel with one of the environment external of the subject, the vacuum pump and the exhaust valve, the secondary insertion element extending between a first end and a second end, and having a bore extending therethrough from the first end to the second end thereof, the first end of the secondary insertion element being adapted for locating in the external vessel, and the second end of the secondary insertion element being adapted for locating in the environment external of the subject.

In another aspect of the invention one of the external vessel pressure sensing means and the external vessel communicating conduit is located in or adjacent the bore of the secondary insertion element. Preferably, the first end of the external vessel communicating conduit terminates in the bore of the secondary insertion element, and advantageously, the external vessel communicating conduit terminates in the bore of the secondary insertion element with the first end of the external vessel communicating conduit substantially coinciding with the first end of the secondary insertion element.

In another aspect of the invention the external vessel pressure sensing means is located in the bore of the secondary insertion element adjacent the first end thereof.

In one aspect of the invention an exhaust conduit is coupled to the second end of the secondary insertion element for exhausting the inflating medium from the external vessel. Preferably, the exhaust conduit couples the one of the vacuum pump and the exhaust valve to the second end of the secondary insertion element.

In one aspect of the invention the external vessel pressure sensing means communicates with the control means, and in another aspect of the invention the external vessel pressure sensing means is hardwired to the control means. Alternatively, the external vessel pressure sensing means communicates with the control means wirelessly, and preferably, through a third wireless communicating means.

In one aspect of the invention the external vessel pressure sensing means comprises a pressure sensor. Advantageously, the external vessel pressure sensing means comprises a miniature pressure sensor, and preferably, the external vessel pressure sensing means comprises a piezoelectric pressure sensor.

In a further aspect of the invention the external vessel pressure sensing means is located in the remote housing.

In one aspect of the invention the inflating medium comprises a gaseous inflating medium.

In one aspect of the invention the inflating medium comprises air, and the source of the inflating medium comprises a compressed air source.

In an alternative aspect of the invention the gaseous inflating medium comprises carbon dioxide.

In another alternative aspect of the invention the inflating medium comprises a liquid inflating medium, for example, a saline solution.

In another aspect of the invention the inflating medium is derived from an inflating medium source. Preferably, the inflating medium is delivered from the inflating medium source to the vessel to be insufflated through an inflating medium control means. Advantageously, the inflating medium control means comprises a flow control valve operable under the control of the control means for controlling the delivery of the inflating medium to the vessel. Preferably, the inflating medium control means comprises a pressure regulating valve for regulating the pressure of the inflating medium from the inflating medium source.

In one aspect of the invention the inflating medium source comprises one of a source of compressed inflating medium, and a pump or a blower for pumping or blowing the inflating medium through the inflating conduit to the vessel. Preferably, the pump or the blower is operated under the control of the control means.

Preferably, each one of the inflating medium source and the inflating medium control means is located in the remote housing.

The invention also provides a system for insufflating a vessel in the body of a human or animal subject, the system comprising the apparatus according to the invention, and the primary insertion element configured for insertion into the vessel to be insufflated.

Preferably, the primary insertion element comprises one of an endoscope and a laparoscope.

In one aspect of the invention the inflating conduit of the apparatus is one of secured to the primary insertion element adjacent a leading end thereof and extends through a bore of the primary insertion element adjacent the leading end thereof for delivering the inflating medium into the vessel to be insufflated.

In another aspect of the invention the primary pressure sensing means is located on the primary insertion element adjacent the leading end thereof.

In another aspect of the invention the carrier element is located in a bore extending through the primary insertion element and extends from the bore adjacent the leading end thereof to extend into an adjacent vessel communicating with the vessel to be insufflated.

The invention also provides a method for controlling insufflation of a vessel in the body of a human or animal subject with a fluid inflating medium, the method comprising monitoring the pressure of the inflating medium in the vessel being insufflated, and controlling delivery of the inflating medium to the vessel being insufflated in response to the monitored pressure of the inflating medium in the vessel.

In one aspect of the invention the pressure being monitored is a pressure substantially identical to the pressure of the inflating medium in the vessel.

In another aspect of the invention the pressure of the inflating medium is monitored directly in the vessel.

In another aspect of the invention delivery of the inflating medium to the vessel is controlled in response to the monitored pressure of the inflating medium in the vessel for maintaining the pressure of the inflating medium in the vessel substantially at a primary predefined pressure.

Preferably, the pressure of the inflating medium in the vessel is monitored by a primary pressure sensing means.

In one aspect of the invention the primary pressure sensing means is located in the vessel.

In an alternative aspect of the invention the primary pressure sensing means is located externally of the vessel, and a primary communicating conduit extending between a first end and a second end and having a bore extending therethrough from the first end to the second end communicates the primary pressure sensing means with the vessel, so that the pressure being monitored by the primary pressure sensing means is substantially identical to the pressure in the vessel.

Preferably, the pressure of the inflating medium in the vessel is controlled by a control means in response to the pressure monitored by the primary pressure sensing means.

Advantageously, delivery of the inflating medium to the vessel is controlled by the control means in response to the pressure monitored by the primary pressure sensing means for maintaining the pressure in the vessel substantially at the primary predefined pressure.

In another aspect of the invention pressure is monitored in a vessel which is adjacent the vessel being insufflated and which communicates with the vessel being insufflated.

In one aspect of the invention one of an alarm signal is produced in response to the monitored pressure in the adjacent vessel reaching an adjacent vessel predefined pressure, and delivery of the inflating medium to the vessel being insufflated is controlled for preventing the pressure in the adjacent vessel exceeding the adjacent vessel predefined pressure in response to the monitored pressure in the adjacent vessel.

Preferably, the pressure in the adjacent vessel is monitored by an adjacent vessel pressure sensing means.

In another aspect of the invention delivery of the inflating medium to the vessel being insufflated is controlled by the control means in response to the pressure monitored by the adjacent vessel pressure sensing means for preventing the pressure in the adjacent vessel exceeding the adjacent vessel predefined pressure.

Advantageously, the alarm signal is produced by the control means in response to the pressure monitored by the adjacent vessel pressure sensing means reaching the adjacent vessel predefined pressure.

In a further aspect of the invention the adjacent vessel pressure sensing means is located in the adjacent vessel.

In an alternative aspect of the invention the adjacent vessel pressure sensing means is located externally of the adjacent vessel, and an adjacent vessel communicating conduit extending between a first end and a second end and having a bore extending therethrough from the first end to the second end communicates the adjacent vessel pressure sensing means with the adjacent vessel, so that the pressure being monitored by the adjacent vessel pressure sensing means is substantially identical to the pressure in the adjacent vessel.

In another aspect of the invention pressure is monitored in a vessel which is external of the vessel being insufflated, and in which the vessel being insufflated is located or is adjoining.

In one aspect of the invention one of the delivery of the inflating medium to the vessel being insufflated is controlled and the external vessel is evacuated or exhausted to atmosphere for preventing the pressure in the external vessel exceeding an external vessel predefined pressure in response to the monitored pressure in the external vessel.

Advantageously, an alarm signal is produced in response to the monitored pressure in the external vessel reaching the external vessel predefined pressure.

Preferably, the pressure in the external vessel is monitored by an external vessel pressure sensing means.

In another aspect of the invention the control means controls evacuation or exhausting of the external vessel in response to the pressure in the external vessel monitored by the external vessel pressure sensing means.

In a further aspect of the invention the control means controls delivery of the inflating medium to the vessel being insufflated in response to the pressure monitored in the external vessel exceeding the external vessel predefined pressure.

In a further aspect of the invention the control means is responsive to the pressure monitored by the external vessel pressure sensing means for producing the alarm signal.

In one aspect of the invention the external vessel pressure sensing means is located in the external vessel.

In an alternative aspect of the invention the external vessel pressure sensing means is located externally of the external vessel, and an external vessel communicating conduit extending between a first end and a second end and having a bore extending therethrough from the first end to the second end thereof communicates the external vessel pressure sensing means with the external vessel, so that the pressure being monitored by the external vessel pressure sensing means is substantially identical to the pressure in the external vessel.

Additionally, the invention provides a method for insufflating a vessel in the body of a human or animal subject, the method comprising delivering a fluid inflating medium into the vessel and controlling insufflation of the vessel by the method according to the invention for controlling insufflation of a vessel being insufflated.

The advantages of the apparatus according to the invention are many. By locating the primary pressure sensing means in the vessel being insufflated, the pressure detected by the primary pressure sensing means is the true pressure of the inflating medium in the insufflated vessel. Therefore, the need to compensate for pressure drops in an inflating conduit between a pressure sensor and the vessel being insufflated due to the fact that the inflating medium is flowing in the inflating conduit is no longer required in order to obtain the actual pressure of the inflating medium in the vessel being insufflated. A particularly important advantage of the invention is that irrespective of leakage of air from the vessel being insufflated, the pressure in the vessel being insufflated is maintained substantially constant at the primary predefined pressure. This is a particularly important advantage of the invention, since leakages from a vessel being insufflated may in many cases be considerable. For example, in the case of the rectum, in general, leakage from the rectum through the anus around the outside of the endoscope or laparoscope is quite common, and leakage from the rectum can also occur through the bore or bores of the endoscope or laparoscope. Furthermore, in the case of resection surgery of the rectum, significant leakage can occur from the rectum into the abdominal cavity. Thus, irrespective of the leakages from the rectum or other vessel being insufflated, the pressure of the inflating medium in the vessel being insufflated is maintained substantially constant at the primary predefined pressure throughout the procedure.

By monitoring the pressure in the external vessel, which is external of the vessel being insufflated and within which the vessel being insufflated is located or is adjoining, the pressure in the external vessel can be controlled, and can be prevented from exceeding the external vessel predefined pressure. Accordingly, there is no danger of the pressure in the external vessel reaching a pressure which could be substantially similar to the pressure within the vessel being insufflated, which would result in the vessel being insufflated collapsing on itself. Additionally, by continuously monitoring the pressure in the external vessel, when the external vessel is the abdominal cavity, and by preventing the pressure in the abdominal cavity exceeding the external vessel predefined pressure, there is little or no risk to patient ventilation, which could otherwise result from hyperinflation of the abdominal cavity, as a result of leakage into the abdominal cavity from the vessel being insufflated.

Additionally, by monitoring the pressure in the adjacent vessel which is adjacent the vessel being insufflated, and which communicates with the vessel being insufflated, there is no danger of hyperinflation of the adjacent vessel. Furthermore, hyperinflation is further prevented by virtue of the fact that the pressure in the adjacent vessel is prevented from exceeding the adjacent vessel predefined pressure. In a case where the vessel being insufflated is the rectum and the adjacent vessel is the colon, by monitoring the pressure in the colon, which communicates directly with the rectum, there is no danger of hyperinflation of the colon.

Figure 2:
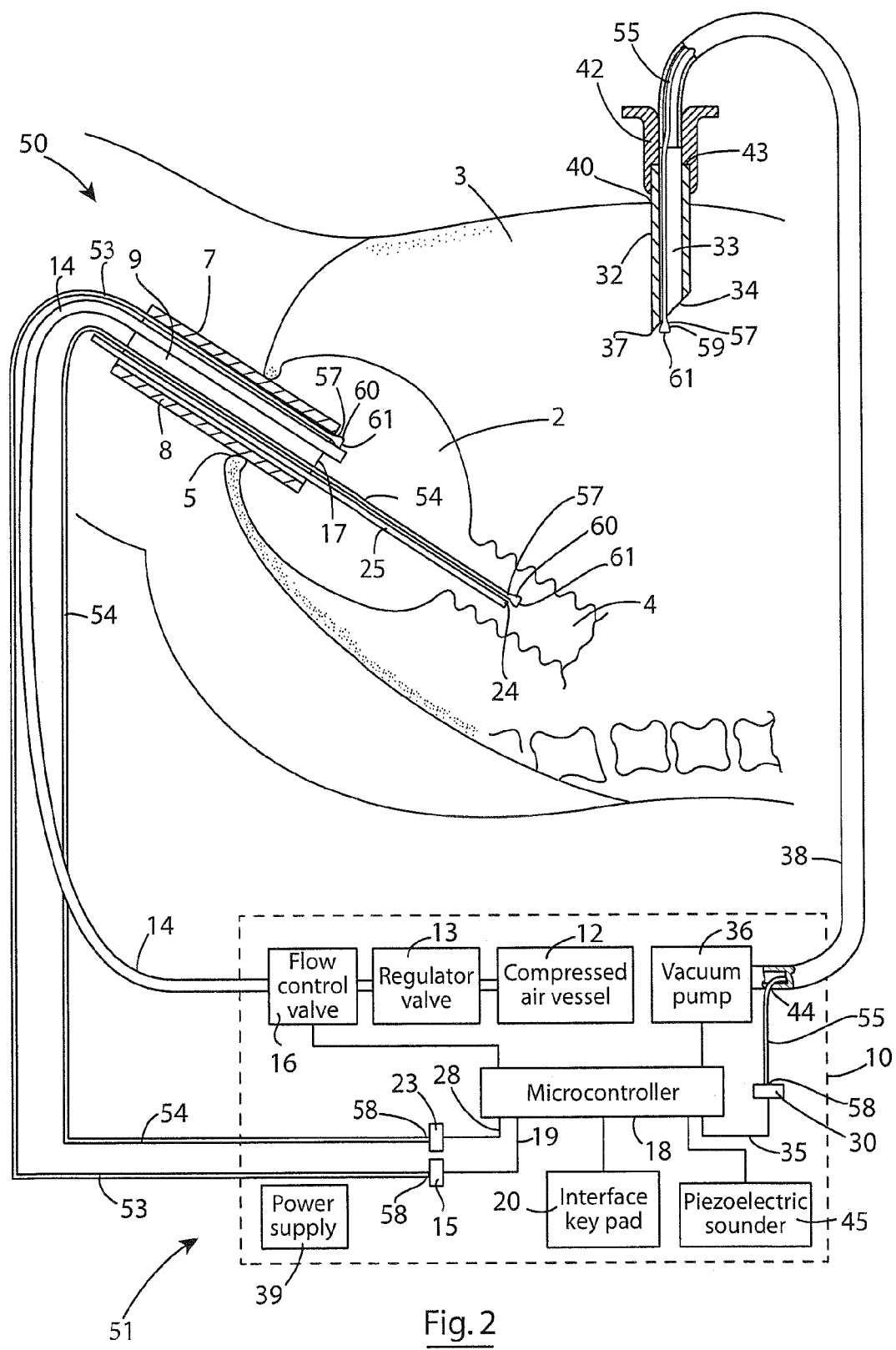
Figure 3:
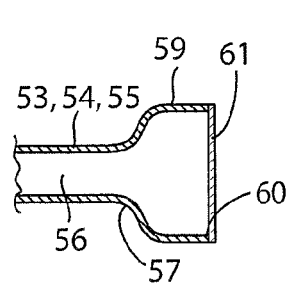
Figure 6:
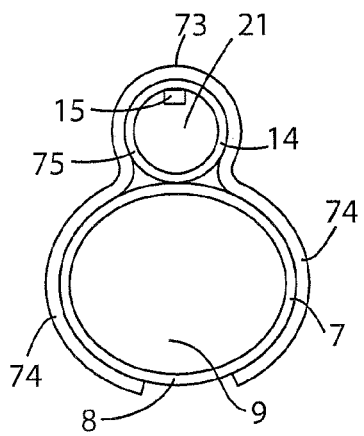
Figure 5:
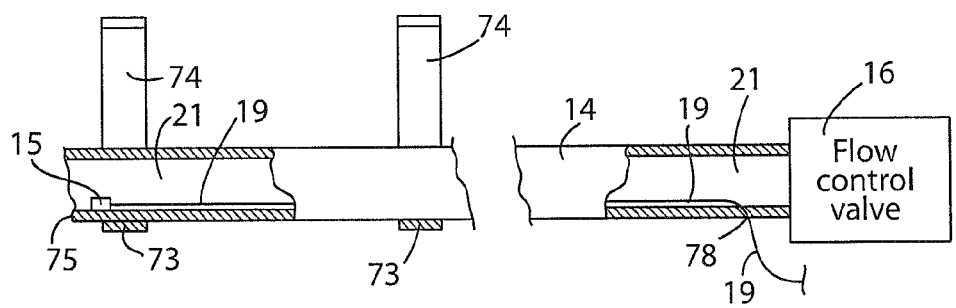
Figure 8:
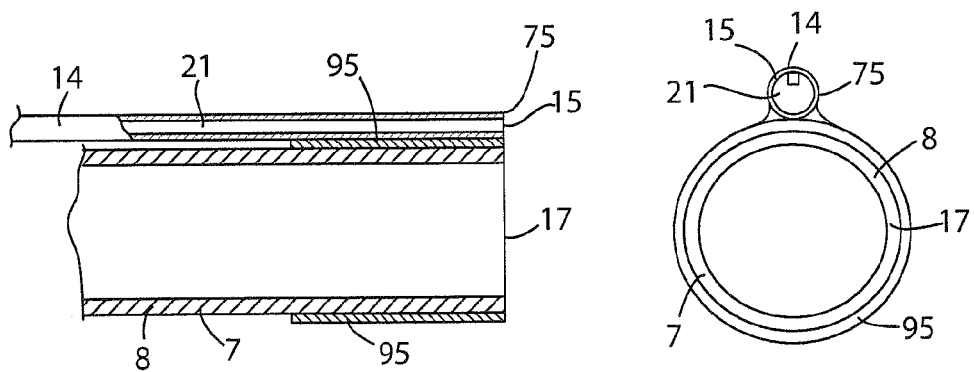
Figure 4:
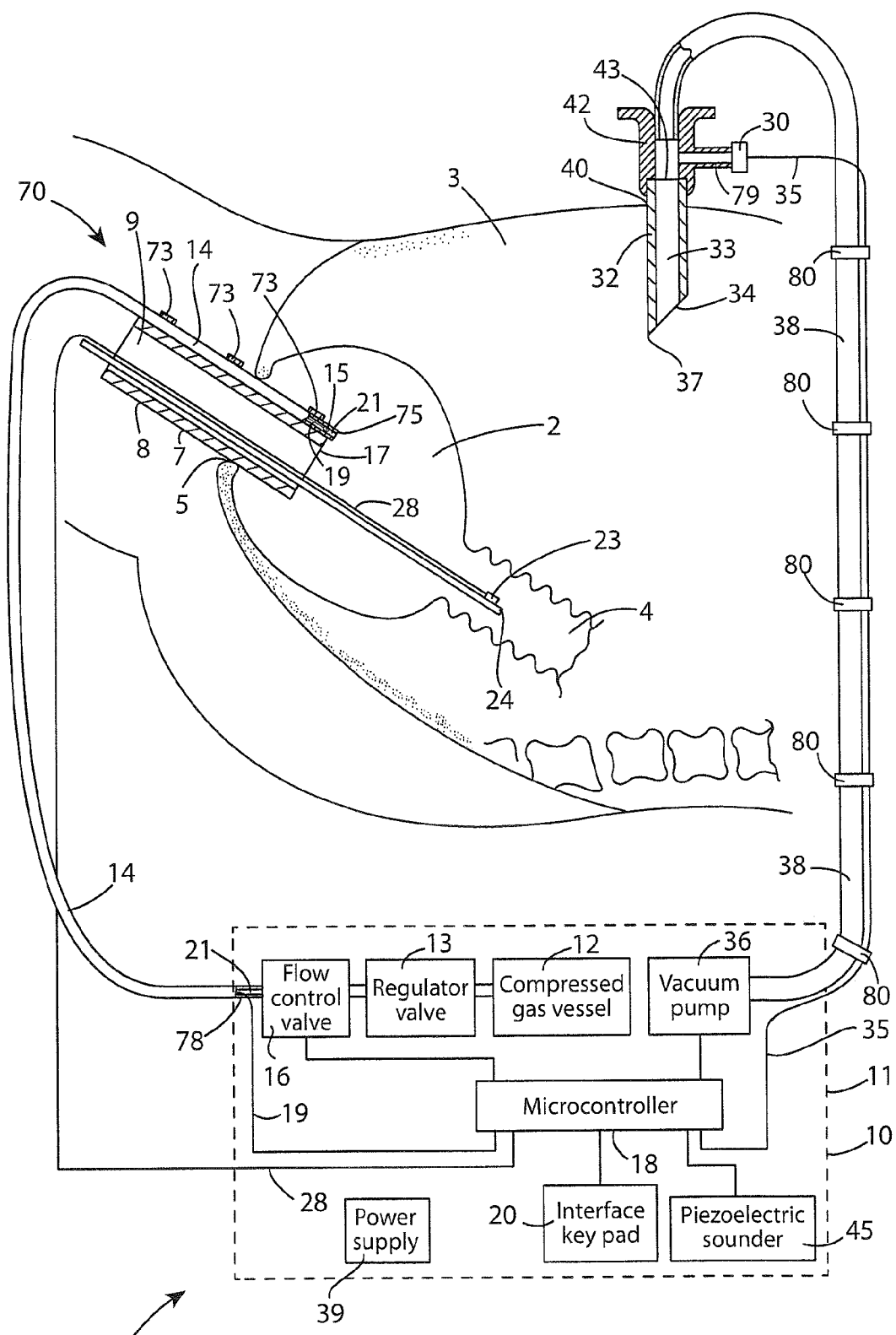
Figure 7:
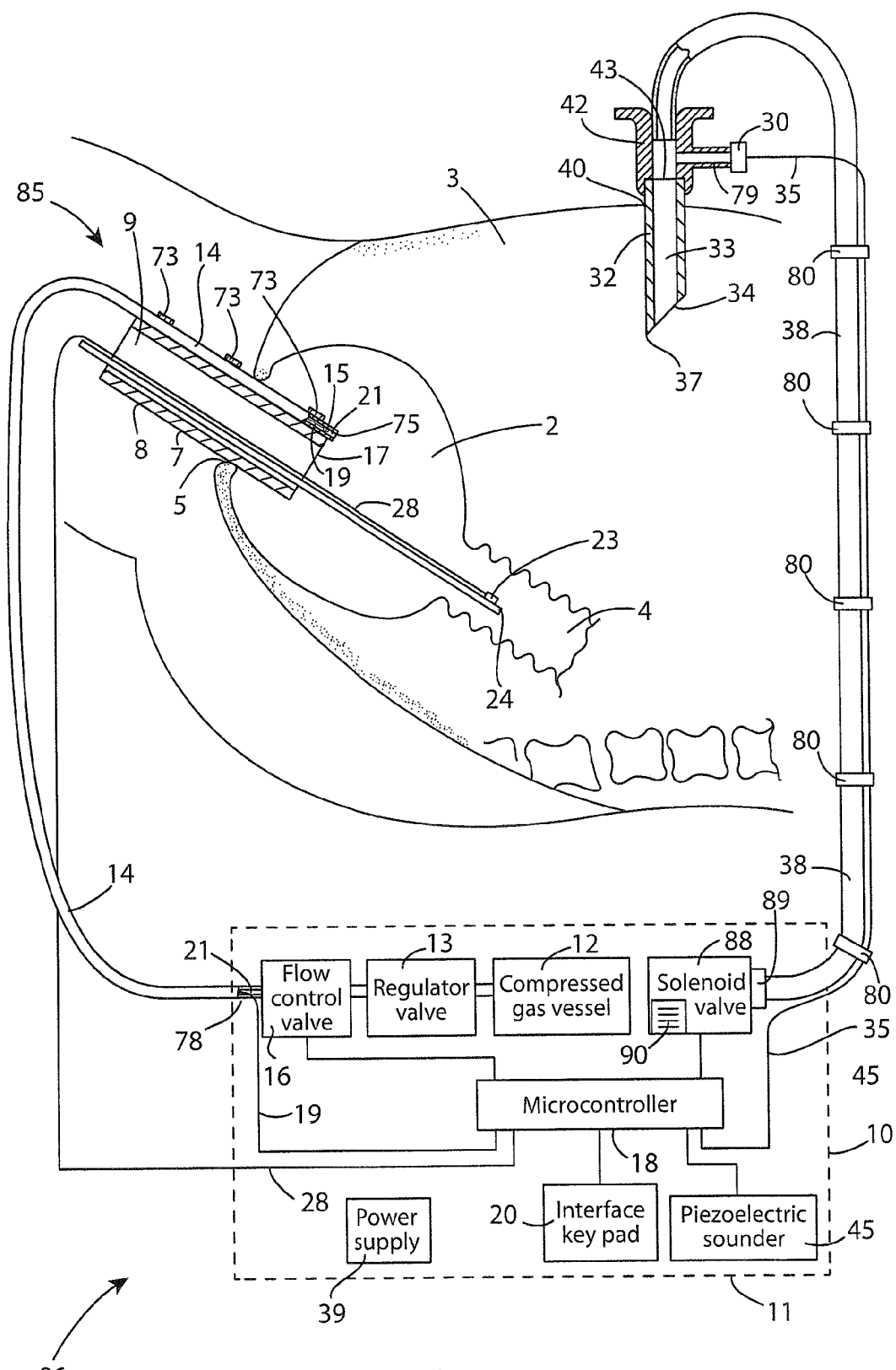

The invention will be more clearly understood from the following description of some preferred embodiments thereof, which are given by way of example only, with reference to the accompanying drawings, in which:

FIG. 1 is a schematic representation, not to scale, of a system according to the invention for insufflating a vessel during a surgical or investigative procedure in a human or animal body, FIG. 2 is a schematic representation, not to scale, of a system according to another embodiment of the invention for insufflating a vessel during a surgical or investigative procedure in a human or animal body, FIG. 3 is a cross-sectional side elevational view of a detail of the system of FIG. 2, FIG. 4 is a schematic representation, not to scale, of a system according to a further embodiment of the invention for insufflating a vessel during a surgical or investigative procedure in a human or animal body, FIG. 5 is an enlarged side view of a detail of the system of FIG. 4, FIG. 6 is an enlarged end view of the detail of FIG. 5 of the system of FIG. 4, FIG. 7 is a schematic representation, not to scale, of a system according to a still further embodiment of the invention for insufflating a vessel during a surgical or investigative procedure in a human or animal body, FIG. 8 is a cross-sectional side elevational view of a detail of apparatus according to the invention for controlling insufflation of a vessel during a surgical or investigative procedure in a human or animal body for use with the systems of FIGS. 4 to 7, and FIG. 9 is an end view of the detail of FIG. 8.

Referring to the drawings and initially to FIG. 1, there is illustrated a system according to the invention indicated generally by the reference numeral 1 for carrying out a method also according to the invention for insufflating a vessel in the body of a human or animal subject, which in this embodiment of the invention is a rectum 2 of a human body, during a surgical or investigative procedure in the rectum 2. The rectum 2 is located in the abdominal cavity 3 between the colon 4 and the anus 5 of the human or animal body, only a portion of the human body is illustrated. The system 1 of FIG. 1 comprises apparatus also according to the invention, indicated generally by the reference numeral 6, for carrying out a method also according to the invention for controlling insufflation of the rectum 2 during insufflation thereof. The system 1 in this embodiment of the invention comprises an elongated primary insertion element 7, which may be an endoscope, a laparoscope or other such similar element, and which in this case is an endoscope 8, only a portion of which is illustrated. The endoscope 8 defines an elongated bore 9 extending therethrough for accommodating, for example, an imaging device for, for example, carrying out an investigative procedure in the rectum 2, and if the primary insertion element 7 is a laparoscope, the bore of the laparoscope would be suitable for accommodating surgical instruments as well as an imaging device, for carrying out surgery on the rectum 2. Such endoscopes and laparoscopes with one or more bores extending therethrough will be known to those skilled in the art, and it is not intended to discuss the primary insertion element 7 in further detail.

The apparatus 6 comprises an insufflator 10 comprising a housing 11, illustrated in broken lines, which houses a fluid inflating medium source, from which fluid inflating medium, in this case air is delivered to the rectum 2 for insufflating thereof. In this embodiment of the invention the fluid inflating medium source comprises a source of compressed air stored in a compressed air vessel 12. Air from the compressed air vessel 12 is delivered to the rectum 2 through an inflating conduit 14. An inflating medium control means for controlling the supply and the pressure at which the air is supplied from the compresses air vessel 12 to the rectum 2 comprises a pressure regulating valve 13 for controlling the pressure at which the inflating air is delivered from the compressed air vessel 12 to the rectum 2, and an electrically operated solenoid or an electric motor operated flow control valve 16 for controlling delivery of the air from the compressed air vessel 12 to the rectum 2. The pressure regulating valve 13 and the flow control valve 16 are located between the compressed air vessel 12 and the inflating conduit 14. Pressure regulated inflating air is delivered through the flow control valve 16 into and through a bore 21 extending through the inflating conduit 14 to the rectum 2. The pressure regulating valve 13 and the flow control valve 16 are housed in the housing 11, and the inflating conduit 14 extends from the housing 11 and is passed into the rectum 2 through the bore 9 in the endoscope 8 for delivering the inflating air to the rectum 2. Typically, inflating air is delivered to the vessel being insufflated at a rate of 1 litre per minute to 20 litres per minute, depending on the vessel and leakage of the air therefrom.

A primary pressure sensing means, namely, a first pressure sensor 15 is recessed into a leading end 17 of the endoscope 8 for directly monitoring the pressure of the inflating air in the rectum 2 adjacent the leading end 17 of the endoscope 8. In this embodiment of the invention the first pressure sensor 15 is a miniature pressure sensor, and preferably, comprises a miniature piezoelectric pressure sensor.

A control means, which in this embodiment of the invention comprises a signal processor, namely, a microcontroller 18 is located in the housing 11 of the insufflator 10, and is electrically coupled to the first pressure sensor 15 by electrically conductive wires 19, so that the microcontroller 18 can read signals from the first pressure sensor 15 which are indicative of the monitored air pressure in the rectum 2 adjacent the leading end 17 of the endoscope 8. The wires 19 from the first pressure sensor 15 extend through the bore 9 of the endoscope 8. The microcontroller 18 is programmed to read the signals from the first pressure sensor 15 and to control the flow control valve 16 for controlling the supply of inflating air from the compressed air vessel 12 to the rectum 2 for in turn maintaining the air pressure in the rectum 2 at a primary predefined pressure, namely, a first predefined pressure. In this embodiment of the invention the first predefined pressure is selectable and is enterable into the microcontroller 18 through an interface 20 located on the housing 11 of the insufflator 10. The interface 20 may be any suitable interface, for example, a keypad interface, a touch screen or the like. The value of the first predefined pressure will be dependent upon the vessel being insufflated, and in particular, will be dependent on the resilience of the vessel being insufflated, and the strength or weakness of the vessel wall. However, typically, the first predefined pressure will lie in the range of 5 mm mercury to 20 mm mercury, and in the case of a rectum, the first predefined pressure would normally be of the order of 15 mm mercury.

An adjacent vessel pressure sensing means, namely, a second pressure sensor 23 is provided for monitoring pressure in a vessel adjacent the vessel being insufflated and which communicates with the vessel being insufflated, and in this case the adjacent vessel is the colon 4. The second pressure sensor 23 is located on a first end 24 of a carrier element 25 which is urgeable through the bore 9 of the endoscope 8 until the first end 24 of the carrier element 25, and in turn the second pressure sensor 23 is located in the colon 4. The second pressure sensor 23 is a miniature pressure sensor, and preferably, comprises a miniature piezoelectric pressure sensor. The carrier element 25 is adapted to be moveable through the bore 9 of the endoscope 8 for facilitating locating of the second pressure sensor 23 at a desired location in the colon 4. Electrically conductive wires 28 extending from the second pressure sensor 23 along the carrier element 25 extend through the bore 9 of the endoscope 8, and in turn are connected to the microcontroller 18, so that the microcontroller 18 can read signals from the second pressure sensor 23 which are indicative of the air pressure in the colon 4.

The microcontroller 18 is programmed to read the signals from the second pressure sensor 23 and to control the operation of the flow control valve 16 for controlling delivery of the air into the rectum 2, so that the air pressure in the colon 4 does not exceed an adjacent vessel predefined pressure, namely, a second predefined pressure. The second predefined pressure is selectable and is enterable into the microcontroller 18 through the interface 20. The value of the second predefined pressure will be dependent upon the nature of the adjacent vessel, and in particular, the strength or weakness of the adjacent vessel wall. However, in general, the second predefined pressure will be higher than the first predefined pressure, and could be up to thirty percent higher than the first predefined pressure. In the case of a colon where the rectum is being insufflated, the second predefined pressure typically will be set at a value of the order of 5 mm mercury above the first predefined pressure.

An external vessel pressure sensing means, namely, a third pressure sensor 30 is provided for monitoring the pressure in a vessel external of the vessel being insufflated and within which the vessel being insufflated is located or is adjoining, and in this case the external vessel comprises the abdominal cavity 3. The third pressure sensor 30 is located in a secondary insertion element, namely, a needle 32 having an elongated bore 33 extending therethrough for monitoring the pressure in the abdominal cavity 3 in the event of a leak from the rectum 2 into the abdominal cavity 3. The third pressure sensor 30 in this embodiment of the invention is a miniature pressure sensor, and preferably, comprises a miniature piezoelectric pressure sensor.

The needle 32 in this embodiment of the invention comprises a Veress needle, which terminates in a first end 34 which is sharpened to a point 37 for penetrating the tissue in the body of a subject for inserting the first end 34 of the needle 32 into the abdominal cavity 3, typically, through the navel 40 of the human body.

The third pressure sensor 30 is located in the bore 33 of the needle 32 adjacent the first end 34 thereof, so that when the first end 34 of the needle 32 is inserted in the abdominal cavity 3, the pressure detected by the third pressure sensor is the true pressure in the abdominal cavity 3. Electrically conductive wire 35 from the third pressure sensor 30 connect the third pressure sensor 30 to the microcontroller 18.

An exhaust conduit 38 for exhausting air from the abdominal cavity 3 is connected to a hub 42 of the needle 32 adjacent a second end 43 of the needle 32. The exhaust conduit 38 terminates in a vacuum pump 36 which is located in the housing 11, and which is operated under the control of the microcontroller 18 for drawing air from the abdominal cavity 3. The wires 35 from the third pressure sensor 30 extend through the exhaust conduit 38 and exit the exhaust conduit 38 through an exit port 44. The wires 35 are sealably located in the exit port 44.

The microcontroller 18 is programmed to read the signals from the third pressure sensor 30 which are indicative of the pressure in the abdominal cavity 3, and to control the operation of either or both of the flow control valve 16 and the vacuum pump 36 for preventing the air pressure in the abdominal cavity 3 exceeding an external vessel predefined pressure, namely, a third predefined pressure in the event of a leak of air into the abdominal cavity 3 from either the rectum 2 or the colon 4. Such a leak from the rectum 2 to the abdominal cavity 3 would typically arise in the event of surgery being carried out in the rectum 2, as will be described below, or as a result of diffusion of the inflating medium through the wall of the vessel being insufflated into the external vessel, for example, in cases where the wall of the vessel being insufflated is permeable to an inflating medium, such as carbon dioxide. The third predefined pressure is selectable and is enterable into the microcontroller 18 through the interface 20. The value of the third predefined pressure will be dependent on the nature of the vessel being insufflated, and the external vessel in which the vessel being insufflated is located or is adjoining. In general, the value of the third predefined pressure will be sufficiently less than the first predefined pressure in order to maintain an adequate pressure difference between the pressure in the vessel being insufflated, and the external vessel in which the vessel being insufflated is located or is adjoining, in order to avoid the vessel being insufflated, collapsing or being inadequately insufflated. Typically, the third predefined pressure will be not more than half the value of the first predefined pressure, and in the case where a rectum is being insufflated the value of the third predefined pressure will be 7 mm mercury or less.

An audible alarm, namely, a piezoelectric sounder 45 is located in the housing 11, and is operable under the control of the microcontroller 18 in response to any one of the pressures monitored by the first, second and third pressure sensors 15, 23 and 30 exceeding the first, second and third predefined pressures, respectively.

A power supply 39 located in the housing 11, which may be powered either by mains electricity or by a battery or by a plurality of batteries in series, which may be rechargeable batteries or non-rechargeable batteries, provides power to the microcontroller 18, the flow control valve 16, the vacuum pump 36, the first, second and third pressure sensors 15, 23 and 30, respectively, and the piezoelectric sounder 45.

In use, when the system 1 is required for insufflating the rectum 2 in order to allow an investigative procedure to be carried out in the rectum 2, only the first and second pressure sensors 15 and 23 are required. Thus, with the first pressure sensor 15 and the second pressure sensor 23 electrically connected to the microcontroller 18, and with the inflating conduit 14 connected to the compressed air vessel 12 through the pressure regulating valve 13 and the flow control valve 16, the system 1 and the apparatus 6 are ready for use. The pressure regulating valve 13 is adjusted to provide the air from the compressed air vessel 12 at a suitable pressure. The values of the first and second predefined pressures are entered into the microcontroller 18 through the interface 20. The endoscope 8 is inserted by its leading end 17 through the anus 5 into the rectum 2 with the leading end 17 of the endoscope 8 located in the rectum 2, and the first pressure sensor 15 on the leading end 17 of the endoscope 8 also located in the rectum 2. The inflating conduit 14 is inserted into the rectum 2 through the bore 9 of the endoscope 8, and the flow control valve 16 is initially operated under the control of the microcontroller 18 for initially insufflating the rectum 2 in order to allow the carrier element 25 to be urged through the rectum 2 into the colon 4. The carrier element 25 with the second pressure sensor 23 located thereon on the first end 24 thereof is urged through the bore 9 of the endoscope 8 through the rectum 2, and in turn into the colon 4 with the second pressure sensor 23 located at a desired location in the colon 4 for directly monitoring air pressure in the colon 4.

The flow control valve 16 is again operated under the control of the microcontroller 18 for maintaining the rectum 2 inflated at the first predefined pressure. During insufflation of the rectum 2, the microcontroller 18 reads the signals from the first pressure sensor 15 which are indicative of the pressure in the rectum 2, and compares the pressure read from the first pressure sensor 15 with the first predefined pressure, and operates the flow control valve 16 in order to maintain the air pressure in the rectum 2 at the first predefined pressure. During insufflating of the rectum 2 the microcontroller 18 also reads the signals from the second pressure sensor 23 which are indicative of the pressure in the colon 4, and compares the pressure read from the second pressure sensor 23 with the second predefined pressure, and operates the flow control valve in order to maintain the pressure in the colon 4 below the second predefined pressure.

On the rectum 2 being insufflated to the first predefined pressure, an imaging device and/or investigative instruments required for carrying out the investigative procedure are inserted through the bore 9 of the endoscope 8 into the rectum 2 in a manner which will be well known to those skilled in the art, and the investigative procedure is carried out on the rectum 2. On completion of the investigative procedure, the imaging device and the investigative instruments are withdrawn from the rectum 2 through the bore 9 of the endoscope 8. The carrier element 25 with the second pressure element 23 thereon is withdrawn from the colon 4 through the rectum 2 and in turn through the bore 9 of the endoscope 8 and the endoscope 8 is then withdrawn from the rectum 2 through the anus 5. As the withdrawal of the endoscope 8 through the anus 5 is just about completed, the flow control valve 16 is operated into the off state for isolating the inflating conduit 14 from the compressed air vessel 12, and the inflating conduit 14 is withdrawn from the rectum 2 with the endoscope 8.

During insufflation of the rectum 2, on the microcontroller 18 determining that the air pressure in the colon 4 has reached the second predefined pressure, or the pressure in the rectum 2 has exceeded the first predefined pressure, the microcontroller 18 operates the piezoelectric sounder 45 to sound an alarm, and operates the flow control valve 16 in order to prevent the air pressure in the colon 4 exceeding the second predefined pressure, and in turn to avoid hyperventilating of the colon 4, and/or to prevent the pressure in the rectum exceeding the first predefined pressure, and likewise to prevent hyperinflating of the rectum 2. When the air pressure in the colon 4 has fallen below the second predefined pressure, and/or the pressure in the rectum 2 has fallen to the first predefined pressure, the microcontroller 18 again operates the flow control valve 16 for maintaining the rectum 2 insufflated at the first predefined pressure.

In the event that the system 1 and the apparatus 6 is to be used in connection with a surgical procedure to be carried out on the rectum 2, and in particular, where a full thickness resection of cancers of the rectum is to be carried out, which would result in leakage of the inflating air from the rectum 2 during insufflating thereof into the abdominal cavity 3, the third pressure sensor 30 is required to monitor the pressure in the abdominal cavity 3. Additionally, in cases where the inflating medium is a gas, for example, carbon dioxide, to which the wall of the vessel being insufflated is permeable, it is also necessary to monitor the pressure in a vessel into which the inflating medium could diffuse from the vessel being insufflated, irrespective of whether the procedure being carried out in the vessel being insufflated is a surgical procedure or an investigative procedure. The value of the third predefined pressure is entered into the microcontroller 18 through the interface 20.

The primary insertion element 7, which in this case would be a laparoscope 8 with the first pressure sensor 15 mounted thereon adjacent the leading end 17 thereof in a similar manner as the first pressure sensor 15 is located adjacent the leading end 17 of the endoscope 8, is inserted through the anus 5 and located in the rectum 2 as already described with reference to the endoscope 8. The inflating conduit 14 is then urged into the rectum 2 through the bore 9 in the laparoscope 8. After initial insufflation of the rectum 2, the carrier element 25 with the second pressure sensor 23 located thereon is urged through the bore 9 in the laparoscope 8 to locate the second pressure sensor 23 in a desired location in the colon 4 also as already described. The needle 32 is inserted through the navel 40 or through any other suitable location in the abdominal wall into the abdominal cavity 3, so that the first end 34 of the needle 32 is located in the abdominal cavity 3 with the third pressure sensor 30 located in the abdominal cavity 3, thereby monitoring the pressure in the abdominal cavity 3. The exhaust conduit 38 extends from the vacuum pump 36 and is connected to the needle 32.

The flow control valve 16 is operated under the control of the microcontroller 18 for insufflating the rectum 2 as already described with reference to the use of the apparatus 6 and the system 1 for carrying out the investigative procedure in the rectum 2.

On the rectum 2 being insufflated to the first predefined pressure, an imaging device and/or surgical implements required for carrying out the resectioning procedure or other surgical procedure are inserted through the bore 9 of the laparoscope 8 into the rectum 2 in a manner which will be well known to those skilled in the art, and the resectioning procedure or other surgical procedure is carried out in the rectum 2. On completion of the surgical procedure, the imaging device and the surgical implements are withdrawn from the rectum 2 through the bore 9 of the laparoscope 8. The carrier element 25 with the second pressure element 23 is withdrawn from the colon 4 through the rectum 2 and in turn through the bore 9 of the laparoscope 8. The laparoscope 8 is then withdrawn from the rectum 2 through the anus 5. As the withdrawal of the laparoscope 8 through the anus 5 is just about completed, the flow control valve 16 is operated into the off state to isolate the inflating conduit 14 from the compressed air vessel 16, and the inflating conduit 14 is withdrawn from the rectum 2 along with the laparoscope 8.

The needle 32 is then withdrawn from the abdominal cavity.

During insufflation of the rectum 2, the microcontroller 18 monitors the signals from the first pressure sensor 15, the second pressure sensor 23 and the third pressure sensor 30 as already described. On the microcontroller 18 determining that the pressure in the rectum 2 exceeds the first predefined pressure, or the pressure in the colon has reached the second predefined pressure, the microcontroller 18 operates the piezoelectric sounder 45 to sound an alarm, and operates the flow control valve 16 for reducing the pressure in the rectum 2 to the first predefined pressure and for reducing the pressure in the colon 4 below the second predefined pressure as already described. Additionally, the microcontroller 18 on determining that the signals read from the third pressure sensor 30 are indicative of the pressure in the abdominal cavity 3 reaching the third predefined pressure, the microcontroller 18 operates the vacuum pump 36 for exhausting air from the abdominal cavity 3 until the air pressure in the abdominal cavity 3 falls below the third predefined pressure. Alternatively, the microcontroller 18, instead of operating only the vacuum pump 36 on the pressure in the abdominal cavity 3 reaching the third predefined pressure, the microcontroller 18 may control the operation of both the vacuum pump 36 and the flow control valve 16 to reduce the pressure in the rectum 2 for in turn reducing the pressure in the abdominal cavity 3 below the third predefined pressure. In which case the microcontroller 18 would operate the vacuum pump 36 first, and if the vacuum pump 36 failed to reduce the pressure in the abdominal cavity 3 below the third predefined pressure, the microcontroller 18 would then operate the flow control valve 16 to reduce the pressure in the rectum 2 until the pressure in the abdominal cavity 3 had fallen below the third predefined pressure. Once the microcontroller 18 has determined that the pressure in the abdominal cavity 3 has fallen below the third predefined pressure, the microcontroller 18 continues to operate the flow control valve 16 for maintaining the pressure in the rectum 2 at the first predefined pressure.

In the event that the microcontroller 18 determines that the pressure in the abdominal cavity 3 cannot be reduced below the third predefined pressure, or in the event of the pressure in the abdominal cavity 3 exceeding the third predefined pressure, the microcontroller 18 is programmed to operate the piezoelectric sounder 45 to sound an alarm, and to operate the flow control valve 16 to reduce the pressure in the rectum 2 to the extent that the pressure in the abdominal cavity 3 commences to fall below the third predefined pressure.

Referring now to FIGS. 2 and 3, there is illustrated a system 50 according to another embodiment of the invention for insufflating a vessel in a human or animal body, which in this embodiment of the invention is also the rectum 2 during a surgical or investigative procedure in the rectum 2. The system 50 comprises apparatus which is also according to another embodiment of the invention and indicated generally by the reference numeral 51 for controlling insufflation of the rectum 2 during the surgical or investigative procedure. Both the system 50 and the apparatus 51 are substantially similar to the system 1 and the apparatus 6, respectively, described with reference to FIG. 1 hereof, and similar components are identified by the same reference numerals, as are similar organs and vessels of the human body likewise identified by the same reference numerals as those in FIG. 1. The system 50 comprises a primary insertion element 7, which in this embodiment of the invention may be an endoscope 8 for carrying out an investigative procedure on the rectum 2, or a laparoscope 8 for carrying out surgery in the rectum 2.

The only difference between the apparatus 51 and the apparatus 6 is that instead of the first, second and third primary sensors 15, 23 and 30 being adapted to be located in the rectum 2, the colon 4 and the abdominal cavity 3, respectively, the first, second and third pressure sensors 15, 23 and 30 are located remotely in the housing 11 of the insufflator 10. In this embodiment of the invention a primary communicating conduit, namely, a first conduit 53 is coupled to the first pressure sensor 15 and extends from the first pressure sensor 15 into the rectum 2 for communicating the first pressure sensor 15 with the rectum 2 so that the pressure monitored by the first pressure sensor 15 is the pressure of the inflating air in the rectum 2. An adjacent vessel communicating conduit, namely, a second conduit 54 is coupled to the second pressure sensor 23 and extends into the adjacent vessel, namely, the colon 4 for communicating the second pressure sensor 23 with the colon 4, so that the pressure monitored by the second pressure sensor 23 is the pressure of the inflating air in the colon 4. An external vessel communicating conduit, namely, a third conduit 55 is coupled to the third pressure sensor 30 and communicates the third pressure sensor 30 with the external vessel, namely, the abdominal cavity 3 so that the pressure monitored by the third pressure sensor 30 is the pressure of air within the abdominal cavity 3.

Each of the first, second and third conduits 53, 54 and 55 extend between a first end 57 and a second end 58 and have a bore 56 extending therethrough from the first end 57 to the second end 58. The second end 58 of each one of the first, second and third conduits 53, 54 and 55 are coupled to the corresponding one of the first, second and third pressure sensors 15, 23 and 30, respectively, with the respective pressure sensors 15, 23 and 30 communicating with the bore 56 in the corresponding one of the first, second and third conduits 53, 54 and 55, respectively.

The second ends 58 of the respective first, second and third conduits 53, 54 and 55 are located in the rectum 2, the colon 4 and the abdominal cavity 3, respectively. The second end 58 of each of the first, second and third conduits 53, 54 and 55 terminates in a diverging cup-shaped element 59 defining an open mouth 60. The open mouth 60 is sealably closed by a flexible membrane 61 which is impermeable to air, and to any other fluids which may be located in the rectum 2, the colon 4 and the abdominal cavity 3. Thus, the bores 56 extending through the first, second and third conduits 53, 54 and 55, respectively, are sealably closed at their respective opposite first and second ends 57 and 58, and contain a static fluid which in this embodiment of the invention is air. The flexible membrane 61 of each of the first, second and third conduits 53, 54 and 55 are sufficiently flexible, so that fluctuations in the pressure in the corresponding one of the rectum 2, the colon 4 and the abdominal cavity 3 induce a corresponding change in pressure in the static fluid in the bore 56 of the corresponding ones of the first, second and third conduits 53, 54 and 55, so that the pressure detected by the first, second and third pressure sensors 15, 23 and 30 is indicative of, and in this embodiment of the invention, identical to the current pressure in the corresponding one of the rectum 2, the colon 4 and the abdominal cavity 3, respectively. Accordingly, although the first, second and third pressure sensors 15, 23 and 30 are remotely located in the housing 11 and are remotely located from the rectum 2, the colon 4 and the abdominal cavity 3, the pressure detected by the first, second and third pressure sensors 15, 23 and 30 is identical to the respective pressures in the rectum 2, the colon 4 and the abdominal cavity 3.

In this embodiment of the invention the first conduit 53 extends from the housing 11 and is passed through the bore 9 of the endoscope 8 or the laparoscope 8, as the case may be, and is secured in the bore 9 to the endoscope 8 or the laparoscope 8 adjacent the leading end 17 thereof, so that the cup-shaped element 59 of the first conduit 53 is located in the rectum 2 adjacent the leading end 17 of the endoscope 8 or the laparoscope 8 in order that the pressure detected by the first pressure sensor 15 is the exact pressure in the rectum 2 adjacent the leading end 17 of the endoscope 8 or the laparoscope 8.

The second conduit 54 extends from the housing 11 and is located on the carrier element 25 with the cup-shaped element 59 located adjacent the first end 24 of the carrier element 25. The carrier element 25 with the second conduit 54 located thereon is passed through the bore 9 of the endoscope 8 or the laparoscope 8 so that the cup element 59 is located in the colon 4, and thus the pressure sensed by the second pressure sensor 23 is identical to the pressure in the colon 4.

The third conduit 55 extends into the exhaust conduit 38 through the exit port 44 and extends through the exhaust conduit 38 and in turn into the bore 33 of the needle 32 with the cup-shaped element 59 of the third conduit 55 located in the bore 33 of the needle 32 adjacent the first end 34 of the needle 32, so that the cup-shaped element 59 of the third conduit 55 is located within the abdominal cavity 3, and the pressure sensed by the third pressure sensor 30 is identical to the pressure in the abdominal cavity 3.

Otherwise, use and operation of the system 50 and the apparatus 51 is similar to use and operation of the system 1 and the apparatus 6, and the advantages achieved by the system 1 and the apparatus 6 are also achieved by the system 50 and the apparatus 51.

Referring now to FIGS. 4 to 6, there is illustrated a system according to another embodiment of the invention, indicated generally by the reference numeral 70, for insufflating a vessel, in this case a rectum 2. The system 70 comprises apparatus also according to the invention, indicated generally by the reference numeral 71, for controlling insufflation of the rectum 2 during insufflation thereof. The system 70 and the apparatus 71 are substantially similar to the system 1 and the apparatus 6, respectively, of FIG. 1 and similar components are identified by the same reference numerals. The main difference between the apparatus 71 and the apparatus 6 lies in the inflating conduit 14 and in the location of the first pressure sensor 15 and the third pressure sensor 30.

The inflating conduit 14 in this embodiment of the invention is configured for releasably securing externally to the primary insertion element 7, which in this case may be an endoscope 8 or a laparoscope 8, and is also configured for extending into the rectum 2 through the anus 5 along with and externally of the endoscope 8 or the laparoscope 8. A releasable conduit coupling means, which in this embodiment of the invention comprises releasable first clips 73 are secured to the inflating conduit 14 for releasably securing the inflating conduit 14 to the endoscope 8 or laparoscope 8 along an outer surface of the endoscope 8 or the laparoscope 8. Each first clip 73 comprises a pair of resilient arcuate limbs 74 for extending around and gripping the outer surface of the endoscope 8 or the laparoscope 8. Typically, the first clips 73 are of a resilient stainless steel material. The inflating conduit 14 terminates in a first end 75, and is clipped onto the endoscope 8 or the laparoscope 8 with the first end 75 located adjacent the leading end 17 of the endoscope 8 or the laparoscope 8.

The first pressure sensor 15 is located in the bore 21 of the inflating conduit 14 adjacent the first end 75 for detecting and monitoring the pressure of the inflating air in the rectum 2 during insufflation thereof. The wires 19 from the first pressure sensor 15 extend through the bore 21 of the inflating conduit 14 and exit the inflating conduit 14 through an exit port 78 adjacent the flow control valve 16. The wires 19 are sealably secured in the exit port 78 in order to avoid leakage of the inflating medium therethrough.

Turning now to the third pressure sensor 30, a port 79 is Teed-off from the hub 42 of the needle 32 and communicates with the bore 33 extending through the needle 32. The third pressure sensor 30, which in this embodiment of the invention may be any suitable pressure sensor and typically is similar to the third pressure sensor 30 of the apparatus of FIG. 1, is sealably mounted on the port 79 and communicates with the bore 33 through the needle 32 for monitoring the pressure in the abdominal cavity 3. The wires 35 from the third pressure sensor 30 are clipped to the exhaust conduit 38 by second clips 80. The second clips 80 secure the wires 35 to the exhaust conduit 38 from the needle 32 to the housing 11 of the insufflator 10.

Additionally, in this embodiment of the invention the compressed gas vessel 12, instead of comprising compressed air, comprises compressed carbon dioxide, and the carbon dioxide from the compressed gas vessel 12 is delivered through the pressure regulating valve 13 where the pressure of the carbon dioxide is regulated and in turn through the flow control valve 16 which is controlled by the microcontroller 18, and in turn through the inflating conduit 14 into the rectum 2.

In use, the inflating conduit 14 is releasably secured to the endoscope 8 or the laparoscope 8, as the case may be by the first clips 73, so that the first end 75 of the inflating conduit 14 substantially coincides with the leading end 17 of the endoscope 8 or the laparoscope 8. With the inflating conduit 14 secured to the endoscope 8 or the laparoscope 8 by the first clips 73, the endoscope 8 or the laparoscope 3 is inserted through the anus 5 into the rectum 2 with the leading end 17 of the endoscope 8 or the laparoscope 8 located in the rectum 2, and with the first end 75 of the inflating conduit 14 located in the rectum 2 adjacent the leading end 17 of the endoscope or the laparoscope 8. The carrier element 25 with the second pressure sensor 23 mounted thereon is inserted through the bore 9 in the endoscope 8 or the laparoscope 8 as already described with reference to the system 1 and apparatus 6 of FIG. 1. The needle 32 if required is then inserted into the abdominal cavity 3 through the navel 40 or through any other suitable part of the abdominal wall.

Otherwise, the system 70 and the apparatus 71 for insufflating and controlling the insufflating of the rectum 2 are similar to the system 1 and the apparatus 6, respectively, described with reference to FIG. 1, and the operation of the system 70 and the apparatus 71 is likewise similar to that already described with reference to the system 1 and apparatus 6 of FIG. 1. Furthermore, the advantages achieved by the system 70 and the apparatus 71 are similar to those achieved by the system 1 and the apparatus 6.

Referring now to FIG. 7, there is illustrated a system according to the invention, indicated generally by the reference numeral 85, for insufflating a vessel, in this case also a rectum 2. The system 85 comprises apparatus also according to the invention, indicated generally by the reference numeral 86, for controlling insufflation of the rectum 2 during insufflation thereof. Both the system 85 and the apparatus 86 are substantially similar to the system 70 and the apparatus 71, respectively, described with reference to FIGS. 4 to 6, and similar components are identified by the same reference numerals.

The main difference between the system 85 and the apparatus 86 and the system 70 and the apparatus 71 is that in the system 85 the vacuum pump 36 has been omitted, and the pressure in the external vessel, namely, the abdominal cavity 3, is controlled by an exhaust valve, which in this embodiment of the invention comprises a solenoid valve 88. The solenoid valve 88 is located in the housing 11, and is operated under the control of the microcontroller 18. The solenoid valve 88 comprises an inlet port 89 which is connected to the needle hub 42 by the exhaust conduit 38, and communicates with the abdominal cavity 3 through the needle 32. An outlet port 90 is provided from the solenoid valve 88 through which gas is exhausted from the abdominal cavity 3.

The solenoid valve 88 is operated under the control of the microcontroller 18 in response to the pressure monitored by the third pressure sensor 30. In this embodiment of the invention the microcontroller 18 is programmed so that on the signals from the third pressure sensor 30 being indicative of the pressure in the abdominal cavity 3 reaching the third predefined pressure, the microcontroller 18 operates the solenoid valve 88 into the open state in order to avoid the pressure in the abdominal cavity 3 exceeding the third predefined pressure. On the signals from the third pressure sensor 30 being indicative of the pressure having dropped below the third predefined pressure, the microcontroller 18 operates the solenoid valve 88 into the closed state, and so operation of the solenoid valve 88 continues under the control of the microcontroller 18 in order to prevent the pressure in the abdominal cavity exceeding the third predefined pressure. In the event of an excessive build-up of pressure in the abdominal cavity 3, the microcontroller 18 is programmed to operate the solenoid valve 88 to exhaust the abdominal cavity 3 and to operate the flow control valve 16 to reduce the pressure in the rectum 2, until the pressure in the abdominal cavity 3 has been reduced below the third predefined pressure.

Otherwise, the system 85 and the apparatus 86 and their operation are similar to the system 70 and the apparatus 71 and their operation described with reference to FIGS. 4 to 6.

An advantage of the system 85 and the apparatus 86 is that both the system 85 and the apparatus 86 is particularly suitable for conserving the inflating medium, particularly when the inflating medium is a gas other than air, for example, carbon dioxide or other such gas. By operating the solenoid valve 88 in the closed state, any inflating medium, for example, carbon dioxide, which leaks or diffuses from the rectum or other vessel being insufflated into the abdominal cavity or other such external vessel is retained in the abdominal cavity or the other external vessel until the pressure in the abdominal cavity or other external vessel reaches the third predefined pressure. Accordingly, as the pressure rises in the abdominal cavity or other such external vessel, the pressure drop between the rectum or other such vessel being insufflated and the abdominal cavity or other such external vessel thereby decreases, which in turn reduces the driving force for urging the inflating medium from the rectum or other such vessel being insufflated into the abdominal cavity or other such external vessel, thereby reducing the leakage of the inflating medium from the rectum or other such vessel being insufflated to the abdominal cavity or other such external vessel. This is particularly so in cases where the inflating medium is a gas to which the wall of the vessel being insufflated is permeable. By reducing the pressure drop across the permeable wall, the rate of diffusion of the inflating medium is significantly reduced.

In an alternative method for operating the system 85 and the apparatus 86, the microcontroller 18 is programmed to retain the solenoid valve 88 in the closed state until the pressure in the abdominal cavity 3 reaches the third predefined pressure. On the pressure in the abdominal cavity 3 reaching the third predefined pressure, the microcontroller 18 operates the solenoid valve 88 into the open state for a predefined time period, which in this embodiment of the invention is approximately three seconds, and then at the end of the three-second predefined time period, the microcontroller 18 operates the solenoid valve 88 from the open state into the closed state. The microcontroller 18 then continues to read the pressure in the abdominal cavity 3 from the third pressure sensor 30, and if the pressure in the abdominal cavity 3 still exceeds the third predefined pressure, the microcontroller operates the solenoid valve 88 from the closed state into the open state for a further one of the predefined time periods of approximately three seconds, and so operation of the solenoid valve 88 continues. However, in the event that the pressure in the abdominal cavity 3 is detected by the microcontroller 18 as continuing to increase above the third predefined pressure, after a predefined number of operations of the solenoid valve 88 into the open state for the predefined time periods each of approximately three seconds, the microcontroller 18 retains the solenoid valve 88 in the open state until the pressure in the abdominal cavity falls below the third predefined pressure. Typically, the solenoid valve 88 would not be continuously operated in the open state until the pressure in the abdominal cavity 3 dropped below the third predefined pressure, until the solenoid valve 88 had been operated into the open state for at least five of the predefined time periods of approximately three seconds each.

As discussed with respect to other embodiments of the invention, the piezoelectric sounder 45 would be operated by the controller 18 in the event that the pressure continued to rise above the third predefined pressure when the valve is continuously operated in the open state, and additionally, the flow control valve 16 would be operated to reduce the flow of the inflating medium to the rectum 2 or to isolate the rectum 2 from the inflating medium until the pressure in the abdominal cavity had dropped below the third predefined pressure.

It will of course be appreciated that while the predefined time periods have been described as being of approximately three seconds, the predefined time periods may be of any suitable duration, and typically, would range between one second and ten seconds, and more typically would range between two seconds and five seconds. Needless to say, the predefined number of times the solenoid valve 88 is operated by the microcontroller into the open state for the respective predefined periods may be any number of times besides five, and typically, the number of times the solenoid valve 88 would be operated into the open state for respective predefined time periods before the solenoid valve would be continuously operated in the open state would lie in the range of three to ten, and more typically would lie in the range of four to eight.

While the valve has been described as a solenoid operated valve, any other suitable valve which would be operable under the control of the microcontroller may be used.

It is envisaged that in certain embodiments of the invention the solenoid valve of the system 85 and apparatus 86 of FIG. 7 may be located adjacent the needle 32, and would be coupled directly to the hub 42 of the needle 32. In which case, the solenoid valve would be electrically connected to the microcontroller 18 by electrically conductive wires, which would extend through the housing 11 to the solenoid valve 88. Alternatively, the solenoid valve 88 may be controlled by the microcontroller by wireless communication.

It is also envisaged that in the embodiment of the apparatus of FIG. 7 the microcontroller 18 may be programmed to operate the solenoid valve 88 between an upper third predefined pressure and a lower third predefined pressure. In which case, the microcontroller 18 would operate the solenoid valve 88 from the closed state to the open state on the pressure read from the third pressure sensor 30 raising to the upper predefined third pressure, and would retain the solenoid valve 88 in the open state until the pressure read from the third pressure sensor 30 fell to the lower predefined third pressure, at which stage the microcontroller 18 would then operate the solenoid valve 88 into the closed state. The microcontroller 18 would retain the solenoid valve in the closed state until the pressure read from the third pressure sensor 30 rose again to the upper third predefined pressure, at which stage the microcontroller 18 would operate the solenoid valve 88 into the open state, and would retain the solenoid valve 88 in the open state until the pressure in the abdominal cavity 3 fell to the lower predefined third pressure. At which stage the microcontroller 18 would operate the solenoid valve 88 into the closed state. And so operation of the solenoid valve 88 would continue under the control of the microcontroller 18.

It will also be appreciated that in the case of the systems and apparatus described with reference to FIGS. 1 to 6, the microcontroller 18 could also be programmed to operate the vacuum pump between an upper third predefined pressure and a lower third predefined pressure. In which case, the vacuum pump 36 would be operated under the control of the microcontroller 18 on the pressure read from the third pressure sensor 30 rising to the upper third predefined pressure, and would be maintained in the operating state until the pressure read from the third pressure sensor had fallen to the lower third predefined pressure, at which stage the vacuum pump 36 would be deactivated by the microcontroller 18, and would not be reactivated by the microcontroller 18 until the pressure read from the third pressure sensor 30 had again risen to the upper third predefined pressure.

Figure 9:
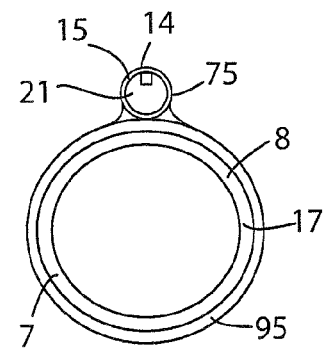

Referring now to FIGS. 8 and 9, there is illustrated a portion of the inflating conduit 14 adjacent the first end 75 thereof of the apparatus 71 and 86 of the systems 70 and 85 of FIGS. 4 to 7. In FIGS. 8 and 9 the inflating conduit 14 is illustrated releasably secured to an endoscope 8 or a laparoscope 8 adjacent the leading end 17 thereof by a releasable conduit coupling means, which in this embodiment of the invention comprises an open-ended sleeve 95 of a resilient material. Any suitable resilient material may be used, however, in this embodiment of the invention the resilient material of the sleeve 95 comprises a silicone material. The sleeve 95 is somewhat similar to a silicone cap of the type which is commonly used in connection with imaging devices in order to prevent contact between the lens of the imaging device and tissue, but with the closed end of the cap removed. In this embodiment of the invention the resilient sleeve 95 is secured to the inflating conduit 14 adjacent the first end 75 thereof by bonding or heat sealing, or alternatively, the sleeve 95 may be integrally formed with the inflating conduit 14. The sleeve 95 is sized so that when resiliently engaged on the endoscope 8 or the laparoscope 8, the sleeve 95 forms a tight friction fit around the endoscope 8 or laparoscope 8 with the inflating conduit 14 extending along the outer surface of the endoscope 8 or laparoscope 8. In this embodiment of the invention the inflating conduit 14 is secured by the sleeve 95 to the endoscope 8 or laparoscope 8 with the first end 75 of the inflating conduit 14 substantially coinciding with the leading end 17 of the endoscope 8 or laparoscope 8.

The resilience of the sleeve 95 is such that although the inflating conduit 14 is tightly secured to the endoscope 8 or the laparoscope 8, nonetheless the sleeve 95 is disengageable and removable from the endoscope 8 or laparoscope 8 when the apparatus 71 or 86 is not required. Needless to say, where the releasable conduit coupling means is provided by a sleeve, the sleeve may be of any other suitable material besides silicone, but in general, the sleeve will be of a resilient material.

While in FIGS. 8 and 9 the inflating conduit 14 is mounted to the exterior of the sleeve 95, the inflating conduit may be mounted internally in the sleeve 95, and in which case the inflating conduit and the endoscope of laparoscope would be sandwiched within the sleeve 95. Indeed, in such a case, the inflating conduit need not necessarily be secured to the sleeve.

It is also envisaged that the first pressure sensor of the apparatus 71 and 86 of FIGS. 4 to 7 may be located in a separate conduit to that of the inflating conduit, and the pressure sensor conduit would be releasably secured to the outer surface of the endoscope or the laparoscope by suitable coupling means, such as a clip or clips, although most likely the inflating conduit and the pressure sensor conduit would be secured together to the endoscope or the laparoscope by a sleeve similar to the sleeve 95 described with reference to FIGS. 8 and 9. It will also be appreciated that the first pressure sensor 15 may be located in the housing 11, and an elongated communicating conduit similar to the first conduit 53 of the apparatus 51 of FIGS. 2 and 3 would be secured to the endoscope or the laparoscope on the outer surface thereof adjacent the leading end thereof in a similar manner as the inflating conduit is secured to the endoscope or laparoscope in FIGS. 8 and 9.

It is envisaged that any other suitable exhaust valve besides a solenoid valve may be provided.

While in the apparatus 1 a first pressure sensor has been described as being located directly on the leading end of the primary insertion element, be it an endoscope, a laparoscope or other such insertion element, the first pressure sensor may be located at any suitable location adjacent the leading end thereof which would result in the first pressure sensor directly monitoring the pressure within the rectum or other vessel in which the surgical or investigative procedure is being carried out.

While the apparatus has been described for maintaining the rectum, in which an investigative or surgical procedure is being carried out, insufflated to allow the procedure to be carried out, it will be readily apparent to those skilled in the art that the apparatus may be used for insufflating any vessel, lumen or cavity in a human or animal body during carrying out of an investigative or surgical procedure in such a vessel, lumen or cavity. For example, it is envisaged that the apparatus and the system may be used for insufflating a colon, an intestine, a stomach, an oesophagus or any other vessel, lumen or cavity in the digestive system of a human or animal subject. The apparatus and the system may also be used for insufflating a vessel, lumen or cavity in the arterial, venal or cardiovascular system of a human or animal subject.

Additionally, the system and the apparatus may be used for insufflating and controlling the insufflation of a lung in which an investigative or surgical procedure is being carried out, and in which case, leakage into the thoracic cavity could arise. In which case the third pressure sensor would be located in the thoracic cavity or would be provided for monitoring the pressure in the thoracic cavity in the event of leakage from the lung being insufflated. Additionally, it is envisaged that the system and apparatus may be provided for insufflating and controlling the insufflation of the thoracic cavity during the carrying out of an investigative or surgical procedure in the thoracic cavity, and in which case, the third pressure sensing means would be located in the abdominal cavity or one or both lungs, or would be provided communicating with the abdominal cavity or one or both lungs for monitoring pressure in the abdominal cavity or the lung or lungs resulting from leakage from the thoracic cavity into the abdominal cavity or the lung or lungs.

While the apparatus has been described as comprising a third pressure sensor, in certain cases, it is envisaged that the third pressure sensor may be omitted. It is also envisaged that in certain cases, the second pressure sensor may be omitted. Indeed, in its basic form the apparatus for controlling insufflation of a vessel will comprise the first pressure sensing means and the control means communicating with each other, and the control means would be configured to control delivery of the inflating medium into the vessel being insufflated. Thus the apparatus according to the invention may be provided with the first pressure sensing means only, or the first pressure sensing means and one of the second and third pressure sensing means, and further the apparatus according to the invention may be provided with the first, second and third pressure sensing means.

While the microcontroller has been described as being responsive to the third pressure sensor for controlling the vacuum pump in order to prevent the air pressure in the abdominal cavity exceeding the third predefined pressure, it is envisaged that the microcontroller may be responsive to the pressure monitored by the third pressure sensor for controlling operation of the flow control valve in order to prevent the pressure within the abdominal cavity exceeding the third predefined pressure. Indeed, in certain cases, it is envisaged that the microcontroller may be responsive to the pressure monitored by the third pressure sensor for operating both the vacuum pump and the flow control valve simultaneously or sequentially for preventing the pressure in the abdominal cavity exceeding the third predefined pressure.

It will be appreciated that while the control means has been described as comprising a microcontroller, any other suitable control means may be provided, which may be any type of signal processor, for example, a microprocessor.

It will also be appreciated that while the first, second and third pressure sensors have been described as being piezoelectric pressure sensors, any other suitable first, second and third pressure sensing means may be provided.

It is also envisaged that while the first, second and third pressure sensors have been described as being hardwired to the microcontroller 18, the signals from the first, second and third pressure sensors indicative of the respective air pressures could be wirelessly communicated to the microcontroller 18, for example, by radio transmitters which could operate under any of the near and medium field communication protocols, for example, a Near Field Communication protocol, Bluetooth or other suitable wireless communications protocol, and signals from the transmitters would be received by a radio receiver communicating with the microcontroller. In which case, the pressure sensors would be provided with suitable wireless transmitters and the microcontroller would be provided with a suitable wireless receiver. Additionally, it is envisaged that the first, second and third pressure sensors may be provided with both a radio receiver and a radio transmitter, and the microcontroller would similarly be provided with a radio receiver and a radio transmitter, so that the microcontroller could communicate with the first, second and third pressure sensors via two-way communication.

In cases where the first, second and third pressure sensors are provided with a radio transmitter or a radio transmitter and a radio receiver, it is envisaged that the first, second and third pressure sensors with their respective radio transmitters or radio transmitters and receivers would be located in the vessel being insufflated, the adjacent vessel and the external vessel, respectively, together with their respective radio transmitters or their respective radio transmitters and receivers. Needless to say, it will be appreciated that the first pressure sensor may be located in the vessel being insufflated by any suitable means, and it is not necessary that the first pressure sensor be located on the endoscope or the laparoscope, or in or on the inflating conduit. It will also be appreciated that any other suitable means may be provided for locating the second and third pressure sensors in the adjacent vessel and the external vessel, respectively, besides locating the second sensor on a carrier element and the third sensor on or in a needle extending into the external vessel.

It is also envisaged that while it is preferable, the first pressure sensing means instead of being located on the primary insertion element adjacent the leading end thereof, the first pressure sensing means could be mounted on a carrier element which would be inserted into the vessel to be insufflated through the primary insertion element, and typically, through the bore 9 of the primary insertion element. The location of the carrier element of the first pressure sensing means in the vessel to be insufflated could be adjusted, so that the first pressure sensing means could be located at the exact location at which the pressure of the inflating air is to be monitored, which typically, would be at a location adjacent the leading end of the primary insertion element.

It will also be appreciated that while the gaseous inflating medium for insufflating the vessel has been described as air or carbon dioxide, any other suitable gaseous inflating medium may be provided. Indeed, in cases where the gaseous inflating medium is air, the air could be delivered to the vessel being insufflated by an air blower or an air pump.

It is also envisaged that in the insufflation of certain vessels in the human or animal body in which an investigative or surgical procedure is being carried out, the inflating medium may be a liquid inflating medium, for example, a saline solution, water or other suitable liquid. In particular, it is envisaged that in the case of insufflating the colon during an investigative or surgical procedure being carried out, the insufflation of the colon may be carried out by delivering a liquid inflating medium to the colon. Needless to say, a liquid inflated medium may also be used in the insufflation of other vessels in a human or animal body.

While the first, second and third conduits of the apparatus 51 have been described as terminating in first ends in cup-shaped elements 59 closed by membranes 61, other suitable arrangement of membranes adjacent the first ends of the tubular elements may be provided to be responsive to pressure fluctuations in the corresponding vessel. Indeed, in certain cases the first end of some or all of the first, second and third conduits may be open to communicate directly with the corresponding vessel. In which case, the fluid in the bore of the tubular element would be the same pressure as the pressure of the fluid in the vessel, and since the fluid in the bore of the first, second and third conduits would be static (not flowing), the pressure detected by the corresponding pressure sensor would be the true pressure of the air or gas in the corresponding vessel.

It is also envisaged that the first conduit may be configured to be secured externally onto the endoscope or laparoscope or other such primary insertion element, and in which case, suitable clips, which would typically be configured for releasably securing the first conduit externally onto the endoscope or laparoscope would be provided.

It will also be appreciated that where the first, second and third conduits are provided closed at both ends, the fluid in the bore may be any suitable fluid, air or other gas, or a liquid.

It is also envisaged that the microcontroller may be configured to store two third predefined pressures, namely, an upper third predefined pressure and a lower third predefined pressure. In which case, it is envisaged that the microcontroller would be configured to control the vacuum pump 36 so that when the pressure in the abdominal cavity, or other such external vessel reached the upper third predefined pressure, the vacuum pump 36 would be operated to evacuate the abdominal cavity, until the pressure monitored by the third pressure sensing means fell to the lower third predefined pressure, at which case, the microcontroller would deactivate the vacuum pump 36 until the pressure monitored by the third pressure sensing means in the abdominal cavity or other such external vessel reached the upper third predefined pressure. Typically, the upper third predefined pressure would be of value of approximately half the first predefined pressure, and the lower third predefined pressure would be of value of approximately one quarter of the first predefined pressure, although needless to say, the upper and lower third predefined pressures may be of any suitable or desirable values.

Additionally, it is envisaged that the first predefined pressure may include an upper first predefined pressure and a lower first predefined pressure, and the second predefined pressure may include an upper second predefined pressure and a lower second predefined pressure. In which case, the microcontroller would operate the flow control valve 16 for maintaining the pressure in the vessel being insufflated within the first and second predefined pressures, and the microcontroller would also operate the vacuum pump or the exhaust valve and/or the flow control valve for maintaining the pressure in the vessel adjacent the vessel being insufflated between the upper and lower second predefined pressures.

It will also be appreciated that the first, second and third predefined pressures, as well as the upper and lower first, second and third predefined pressures, as appropriate, may be pre-programmed into the microcontroller.

While the alarm means has been described as comprising an audible alarm, the alarm means may be provided as well as or instead of an audible alarm by a visual alarm, for example, a light which would provide a visually perceptible signal or any other such device which would provide a visually perceptible signal. For example, in cases where the interface means comprises a touch screen, the touch screen could be configured to flash in response to an alarm signal. It will also be appreciated that any other suitable audible alarm besides a piezoelectric sounder may be provided.

The invention claimed is:

1. Apparatus for controlling insufflation of a vessel in a body of a human or animal subject with a fluid inflating medium, the apparatus comprising:
a primary insertion element adapted for insertion into the vessel being insufflated, the primary insertion element having a bore extending therethrough for communicating with the vessel being insufflated,
a primary pressure sensing means configured for monitoring pressure of the inflating medium in the vessel being insufflated,
an adjacent vessel pressure sensing means for monitoring pressure of the inflating medium in an adjacent vessel, the adjacent vessel being adjacent the vessel being insufflated and communicating with the vessel being insufflated,
a carrier element terminating in a first end,
the adjacent vessel pressure sensing means being mounted on the carrier element adjacent the first end thereof,
the carrier element being located in the bore of the primary insertion element and being urgeable longitudinally through the bore of the primary insertion element and through the vessel being insufflated into the adjacent vessel with the first end thereof located in the adjacent vessel,
a control means for controlling delivery of the inflating medium to the vessel being insufflated in response to the pressure in the vessel being insufflated that is monitored by the primary pressure sensing means, and
the control means is responsive to the pressure of the inflating medium in the adjacent vessel that is monitored by the adjacent vessel pressure sensing means for
producing an alarm signal in response to the pressure in the adjacent vessel reaching an adjacent vessel predefined pressure, or
controlling delivery of the inflating medium to the vessel being insufflated for preventing the pressure in the adjacent vessel exceeding the adjacent vessel predefined pressure.

2. Apparatus as claimed in claim 1 in which the primary pressure sensing means is configured for monitoring the pressure of the inflating medium in the vessel being insufflated adjacent a leading end of the primary insertion element.

3. Apparatus as claimed in claim 1 in which the primary pressure sensing means is adapted for locating in the vessel.

4. Apparatus as claimed in claim 1 in which the primary pressure sensing means is adapted for locating remotely of the vessel, and a primary communicating conduit extending between a first end and a second end and having a bore extending therethrough between the first end and the second end thereof is provided, the first end of the primary communicating conduit being adapted to extend into the vessel, and the second end thereof being coupled to the primary pressure sensing means with the primary pressure sensing means communicating with the bore of the primary communicating conduit, a static fluid being located in the bore of the primary communicating conduit, and pressure of the static fluid in the bore of the primary communicating conduit being indicative of the pressure of the inflating medium in the vessel.

5. Apparatus as claimed in claim 4 in which the first end of the primary communicating conduit terminates in a flexible membrane configured to flex relative to the primary communicating conduit in response to pressure fluctuation of the inflating medium in the vessel for in turn proportionately varying the pressure of the static fluid in the bore of the primary communicating conduit.

6. Apparatus as claimed in claim 1 in which the apparatus further comprises:
an external vessel pressure sensing means for monitoring pressure in an external vessel that is located externally of the vessel being insufflated, but is adjoining the vessel being insufflated, or the vessel being insufflated is located within the external vessel, and
the control means is responsive to the external vessel pressure sensing means for
producing an alarm signal in response to the pressure in the external vessel reaching an external vessel predefined pressure, or
controlling one of delivery of the inflating medium to the vessel being insufflated, a vacuum pump communicating with the external vessel, and an exhaust valve communicating with the external vessel for preventing the pressure in the external vessel exceeding the external vessel predefined pressure.

7. Apparatus as claimed in claim 6 in which the external vessel pressure sensing means is adapted for locating in the external vessel.

8. Apparatus as claimed in claim 6 in which a secondary insertion element is provided for inserting into the external vessel to communicate the external vessel with one of an environment external of the subject, the vacuum pump and the exhaust valve, the secondary insertion element extending between a first end and a second end, and having a bore extending therethrough from the first end to the second end thereof, the first end of the secondary insertion element being adapted for locating in the external vessel, and the second end of the secondary insertion element being adapted for locating in the environment external of the subject, communicating with the vacuum pump or communicating with the exhaust valve.

9. Apparatus as claimed in claim 8 in which an external vessel communicating conduit extending between a first end and a second end and having a bore extending between the first and second ends thereof is provided, the first end of the external vessel communicating conduit being configured to extend into the external vessel, and the second end being coupled to the external vessel pressure sensing means with the external vessel pressure sensing means communicating with the bore of the external vessel communicating conduit, a static fluid being located in the bore of the external vessel communicating conduit, and pressure in the static fluid in the bore of the external vessel communicating conduit being indicative of the pressure in the external vessel.

10. Apparatus as claimed in claim 9 in which the external vessel communicating conduit is located in or adjacent the bore of the secondary insertion element.

11. Apparatus as claimed in claim 9 in which the first end of the external vessel communicating conduit terminates in the bore of the secondary insertion element.

12. Apparatus as claimed in claim 8 in which the external vessel pressure sensing means is located in or adjacent the bore of the secondary insertion element.

13. Apparatus as claimed in claim 8 in which an exhaust conduit is coupled to the second end of the secondary insertion element for exhausting the inflating medium from the external vessel, the exhaust conduit communicating the one of the vacuum pump and the exhaust valve with the second end of the secondary insertion element.

14. Apparatus as claimed in claim 6 in which the external vessel pressure sensing means is adapted for locating remotely of the external vessel.

15. Apparatus as claimed in claim 6 in which the control means is responsive to the external vessel pressure sensing means for producing the alarm signal in response to the pressure in the external vessel reaching the external vessel predefined pressure.

16. Apparatus as claimed in claim 1 in which the adjacent vessel pressure sensing means comprises a miniature pressure sensor.

17. Apparatus as claimed in claim 1 in which the adjacent vessel pressure sensing means comprises a piezoelectric pressure sensor.

* * * * *